US005736508A

United States Patent [19]
McMichael

[11] Patent Number: 5,736,508
[45] Date of Patent: Apr. 7, 1998

[54] METHODS FOR TREATMENT OF SCAR TISSUE

[75] Inventor: John McMichael, Delanson, N.Y.

[73] Assignee: Milkhaus Laboratory, Inc., Delanson, N.Y.

[21] Appl. No.: 811,347

[22] Filed: Mar. 4, 1997

[51] Int. Cl.⁶ .................................................. A61K 38/00
[52] U.S. Cl. .................................................. 514/2; 514/23
[58] Field of Search .................................. 514/2, 23

[56] References Cited

U.S. PATENT DOCUMENTS 5,378,620  1/1995  Adams et al. ........................ 435/183
5,576,289  11/1996  McMichael .......................... 514/2

OTHER PUBLICATIONS

Razin et al., *Proc. Nat'l. Acad. Sci. (USA),* 91:7722–7726 (1994).

Kaplan E.L.et al. J. Exp. Med., 144(3): 754–767, Mar. 1976.

Pashinyan E.R. et al. Zh. Exper. Klin. Med. (Russ). 22 (5):444–450, May 1982.

*Primary Examiner*—Cecilia J. Tsang
*Assistant Examiner*—Michael Borin
*Attorney, Agent, or Firm*—Marshall, O'Toole, Gerstein, Murray & Borun

[57] ABSTRACT

Methods are presented for treatment in eliminating or reducing the appearance of scar tissue by administration of streptolysin O.

12 Claims, No Drawings

METHODS FOR TREATMENT OF SCAR TISSUE

FIELD OF THE INVENTION

The present invention relates generally to methods for treating and reducing the appearance of scar tissue with streptolysin O.

BACKGROUND OF THE INVENTION

Streptolysin O is one of a group of filterable hemolysins derived from Group A beta-hemolytic streptococci. Specifically, streptolysin O is a 60kD peptide which is hemolytic in its reduced state but is inactivated upon oxidation. Streptolysin O is used in the art generally as an analytical reagent for permeabilizing cells. See, e.g., Razin et al., *Proc. Nat'l. Acad. Sci.* (USA), 91:7722–7726 (1994). Co-owned U.S. Pat. No. 5,576,289, the disclosure of which is hereby incorporated by reference, discloses the use of streptolysin O in methods for treating disease states characterized by motor deficit. No disclosure is made of utility of streptolysin O in treating scarring, however.

Scarring is caused by excess production of collagen during healing. Collagen is the major structural protein of skin and is responsible for its tensile strength, elasticity, and pliability. It is synthesized in the dermis by fibroblasts. The healing of a wound is a series of complex biological events taking place over an extended period of time. When tissue is cut, the edges of the wound separate and pull apart by the elasticity of the skin. Blood from severed blood vessels fills the cavity of the wound. The blood clots dry, and become hard, forming a scab. The scab shrinks during the first 24 hours, drawing the edges of the wound closer together. Gradually, a grayish, thin membrane extends out from the skin edge and covers the whole wound surface after the scab falls off. The area of the wound is steadily reduced by a process of contraction until there is no raw surface area.

The scar surface area gradually fades until it is paler than the surrounding skin. The process of contraction continues even after the scar is formed as is shown by the gradual shortening of the wound. Some wounds during healing will cross normal skin lines and become depressed below the level of the surrounding skin.

On a microscopic scale, the wound-healing process consists of the development of fibrin which causes the blood clot to contract. White cells arrive at the wound site and macrophages digest debris present in the wound. Growth of blood capillaries is followed by the inward growth of fibrous tissue migrating from the cells on the wound's margin area. The developing fibrous tissue increases and eventually fills the wound cavity with a network of interlacing threads of collagen that finally arrange themselves in firm bands.

During this process, the surface area of the wound becomes covered by a process of enlargement, flattening, and multiplication of the preexisting epithelial skin cells at the edge of the wound. The epithelial cells divide and spread down into the wound and eventually cause the wound to coalesce to perfect healing.

Once scarring has occurred, it cannot be reversed, although considerable shrinking or reduction of the scarring may occur. Typically, scars do not tan in sunlight, nor do they produce hair or sweat. These characteristics are evidence that the skin has failed to return to its full function.

The present invention provides methods for treating patients with streptolysin O to prevent or reduce the appearance of scar tissue such as caused by surgical, acne, burns, and trauma-induced scarring.

SUMMARY OF THE INVENTION

The present invention provides methods for treating and reducing the appearance of scar tissue and for promoting wound healing and to preventing formation of scar tissue. Methods of the invention result in the reduction of the unsightly appearance of scar tissue such as caused by surgery, acne, burns, trauma-induced injury, and the like. The invention comprises the step of administering an effective amount of streptolysin O to a subject seeking to reduce the appearance of already formed scar tissue, or to promote the healing of a wound after surgery so as to prevent or minimize scarring. The precise dose will vary among patients and may readily be determined by experiments. Nevertheless, preferred dosages generally range from about 0.0032 units to about 50 units with dosages of from 0.01 units to 10 units being preferred. Streptolysin O may be administered by a variety of routes including intravenous, intramuscular, subcutaneous, intrathecal, and oral routes of administration with sublingual administration being preferred. It is also anticipated that alternative routes of administration may be by inhalation and topical application. If administered sublingually, it is preferred that streptolysin be administered 1–10 drops (0.05 ml per drop) per day with a dosage of from about 0.01 to about 10 units per drop.

Treatment methods according to the invention are effective against any scar tissue, including, but not limited to, surgical scars, acne scars, trauma-induced scars, and burn scars. The compositions of the invention are also effective in promoting the healing process resulting in little or no scarring, when taken just prior to surgery and continued for a time following surgery. Additional aspects and advantages of the invention will become apparent upon consideration of the following detailed description thereof.

DETAILED DESCRIPTION OF THE INVENTION

The present invention relates to the discovery that treatment of a patient with streptolysin O can reduce or eliminate the appearance of scarring. It has also been discovered that such treatment prior to and after surgery will promote the healing of the skin and reduce or eliminate resultant scarring. Administration of streptolysin O has also been shown to be effective in reducing the fine lines and wrinkles of the skin, including stretch marks. Examples of human clinical uses and the results thereof are presented herein. In each case, clinical histories of the patients were known or taken prior to treatment with streptolysin O for other purposes and evaluations of the patient's comments were recorded during the course of treatment. In the reported examples, patients were being treated with streptolysin O for other reasons and coincidentally observed remarkable reduction in the appearance of scarring and wrinkles. Enhanced healing after surgery was also observed, including reduced or no scarring. In stone cases, tightness and restricted movement resulting from scar tissue formation were reduced.

In the present invention, patients were treated using relatively low doses of streptolysin O. A preferred route of administration is sublingually and patients were generally instructed to self-administer from one to about 6 drops daily. Each drop contains from about 0.016 units to about 10 units of streptolysin O, with 2 units being preferred. The precise dosage for each patient was determined by the degree of sensitivity displayed in a modified test for allergy to streptolysin O.

Subjects were initially tested to determine the extent of any allergic response which might be observed by application of small amounts of streptolysin O by either intradermal, sublingual, intravenous, or other suitable means. Testing dosages can range from an initial concentration of 0.0032 units to a maximum of 50 units. Subcutaneous injections may also be administered, preferably in the form of 1 or 2 injections a day. Proper dosing of a composition according to the present invention may easily be determined by the skilled artisan using standard procedures and upon evaluation of the severity of a patient's symptoms. Streptolysin O for use in methods according to the invention may be formulated in an appropriate vehicle, including water, saline, dextrose, and albumin.

Provided below are case histories of patients being treated with streptolysin O for other medical purposes which provide evidence of the effectiveness of the treatment methods described herein. Noticeable reduction in scarring was observed in some cases, while enhanced wound healing after surgery was observed in others. The reduction of facial lines and wrinkles were also observed.

The following Examples are intended to illustrate practice of the preferred embodiments of the invention. Numerous additional embodiments and improvements are apparent upon consideration of the following Examples.

EXAMPLE I

A 53-year-old physician had knee surgery and was treated by administering 2 units of streptolysin O per drop (0.05 ml) four times daily. The patient reported "remarkable" recovery without scarring. Treatment was initiated on the day of surgery and discontinued after three weeks.

EXAMPLE II

A 55-year-old nurse had abdominal surgery and was treated by administration of streptolysin O according to Example I. At her 10-day follow-up office visit, the surgeon examined her and was initially unable to determine the site of the surgery. The patient was surprised at the advanced state of healing, lack of scarring, and lack of evidence of surgical invasion.

EXAMPLE III

A 62-year-old man was treated using streptolysin O according to Example I at the rate of 1 drop 3-4 times per day. After four weeks, the subject observed significant reduction of facial acne scars present since adolescence.

EXAMPLE IV

According to this example, a male patient's facial lines and wrinkles were observed to fade after a regimen of sublingual administration of three drops per day containing 2 units of streptolysin O per drop for one month.

EXAMPLE V

A female patient reported that visceral adhesions in her abdomen and pelvis had faded and patterns of pain had improved. According to this example, the patient had burn scars on her hand and was treated by sublingual administration according to Example I. After 30 days, the burn scars on her hands had faded and the dorsum of the other hand was entirely clear with minimal scarring remaining between her knuckles.

EXAMPLE VI

A female patient was treated with one drop of streptolysin O according to Example I three to four times per day. After three weeks of treatment, severe acne scarring on her chin was observed to have softened. She reported improved ability to move her mouth without the tightness caused by the scarring.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method for reducing the appearance of scar tissue in a subject comprising the step of:

administering to said subject an effective amount of streptolysin O in a pharmaceutically acceptable vehicle.

2. The method according to claim 1 wherein said streptolysin O is administered by a method selected from the group consisting of intramuscular, sublingual, intravenous, subcutaneous, intrathecal, inhalation, and topical.

3. The method according to claim 1 wherein said streptolysin O is administered to said patient sublingually in a dose from about 0.0032 units to about 50 units.

4. The method according to claim 1 wherein said streptolysin O is administered to said patient sublingually in a dose from about 0.01 units to about 10 units.

5. A method for promoting the healing of a wound of a subject comprising the step of:

administering to said subject an effective amount of streptolysin O in a pharmaceutically acceptable vehicle.

6. The method according to claim 5 wherein said streptolysin O is administered by a method selected from the group consisting of intramuscular, sublingual, intravenous, subcutaneous, intrathecal, inhalation, and topical.

7. The method according to claim 5 wherein said streptolysin O is administered to said patient sublingually in a dose from about 0.0032 units to about 50 units.

8. The method according to claim 5 wherein said streptolysin O is administered to said patient sublingually in a dose from about 0.01 units to about 10 units.

9. A method for reducing the appearance of fine lines, wrinkles, and stretch marks on the skin of a subject comprising the step of:

administering to said subject an effective amount of streptolysin O in a pharmaceutically acceptable vehicle.

10. The method according to claim 9 wherein said streptolysin O is administered by a method selected from the group consisting of intramuscular, sublingual, intravenous, subcutaneous, intrathecal, inhalation, and topical.

11. The method according to claim 10 wherein said streptolysin O is administered to said patient sublingually in a dose from about 0.0032 units to about 50 units.

12. The method according to claim 11 wherein said streptolysin O is administered to said patient sublingually in a dose from about 0.01 units to about 10 units.

* * * * *

UNITED STATES PATENT AND TRADEMARK OFFICE
CERTIFICATE OF CORRECTION

PATENT NO. : 5,736,508

DATED : April 7, 1998

INVENTOR(S) : John McMichael

It is certified that error appears in the above-identified patent and that said Letters Patent is hereby corrected as shown below:

Column 2, line 55, "stone" should be --some--

Signed and Sealed this

Twenty-seventh Day of July, 1999

Attest:

Attesting Officer

Q. TODD DICKINSON

Acting Commissioner of Patents and Trademarks